United States Patent [19]
Platt

[11] Patent Number: 5,641,753
[45] Date of Patent: Jun. 24, 1997

[54] 10-AZA-9-DEOXO-11-DEOXY-ERYTHROMYCIN A AND DERIVATIVES COMBINED WITH SULFISOXAZOLE

[75] Inventor: Chris Platt, Huntington Beach, Calif.

[73] Assignee: Chris E. Platt, Huntington Beach, Calif.

[21] Appl. No.: 622,250

[22] Filed: Mar. 25, 1996

[51] Int. Cl.$^6$ .................... A61K 31/70; C07H 17/08
[52] U.S. Cl. .................... 514/29; 435/34; 435/18; 435/29; 435/39; 435/40; 435/51; 536/7.2
[58] Field of Search .................... 435/34, 18, 29, 435/39, 40, 51; 536/7.2; 514/29

[56] References Cited

PUBLICATIONS

Tarpay et al., Antimicrobial Agents and Chemotherapy, vol. 22, No. 1, pp. 145–147 (1982).
Hughes et al., J. of Infectious Diseases, vol. 170, No. 1, pp. 906–911, (1994).
Doern et al., Antimicrobial Agents and Chemotherapy, vol. 32, No. 2, pp. 180–185 (1988).

*Primary Examiner*—James O. Wilson
*Attorney, Agent, or Firm*—Gene Scott; James O Neill

[57] ABSTRACT

Pharmaceutical compositions of an erythromycin derivative combined with sulfisoxazole according to the structural formulas:

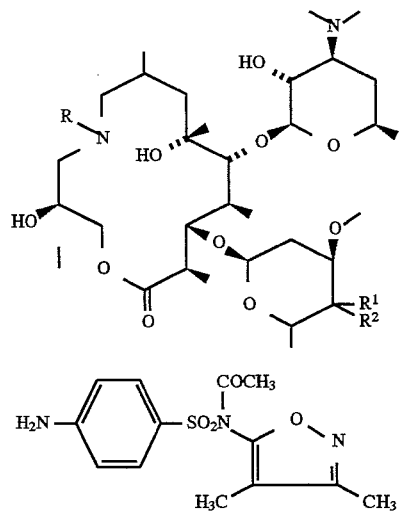

where R is hydrogen, C1–C10 alkylcarbonyl or C1–C10 alkyl wherein the substituent is amino or cyano; R1 and R2 are independently hydrogen, hydroxyl or amino; and the pharmaceutical salts and esters thereof.

5 Claims, No Drawings

10-AZA-9-DEOXO-11-DEOXY-ERYTHROMYCIN A AND DERIVATIVES COMBINED WITH SULFISOXAZOLE

BACKGROUND OF THE INVENTION

1. Field of the Invention

The present invention relates to a novel group of chemical compounds providing antibacterial activity, and which are useful in the therapy of bacterial infections in mammals. More specifically, the invention relates to compositions including the derivatives of the well-known antibiotic, erythromycin A.

2. Description of Related Art

The related art includes:

Tarpay et al, Antimicrobial Agents and Chemotherapy, Vol. 22, No. 1, pages 145–147 (1982).

Hughes et al., J. of Infectious Diseases, Vol. 170, No. 1, pages 906–911, (1994).

Doern et al., Antimicrobial Agents and Chemotherapy, Vol. 32, No. 2, pages 180–185 (1988).

U.S. Pat. Nos.:

| | |
|---|---|
| 4,328,334 to Korbrehel et al | 4,464,527 to Bright et al |
| 4,465,674 to Bright et al | 4,492,688 to Bright et al |
| 4,512,982 to Hanske et al | 4,517,359 to Kobrehel et al |
| 4,526,889 to Bright et al | 4,518,590 to Hanske et al |
| 4,886,792 to Djokie | 4,957,905 to Hunt et al |

SUMMARY OF THE INVENTION

The erythromycin derivatives act by binding to the 50S ribosomal subunit of susceptible microorganisms and, thus, interfere with microbial protein synthesis. Nucleic acid synthesis is not affected. The sulfisoxazole inhibits bacterial synthesis of dihydrofolic acid by preventing the condensation of the pteridine with para-aminobenzoic acid through competitive inhibition of the enzyme dihydopteroate synthetase. After absorption the erythromycin derivative is largely bound to plasma proteins and readily diffuses into most body fluids. Rapid distribution of erythromycin derivative into tissues and high concentration within cells results in higher concentrations in tissues than in serum or plasma. Erythromycin derivative seems to concentrate in fibroblasts and phagocytes as demonstrated by in vivo incubation techniques. Such derivatives are modifications of the well-known antibiotic, erythromycin A, having the following structure:

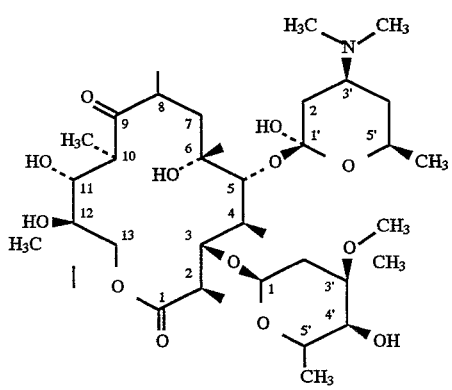

The erythromycin derivatives of the present invention relate to the compounds of the following structure and derivatives thereof, which form a novel class of 14-membered azalides characterized in that the heterocyclic nitrogen atom is situated at the 10 position. The inventive step in the present invention is that these compounds are combined with sulfisoxazole for enhanced antibacterial activity. The present invention provides for novel pharmaceutical compositions and methods for their use as antibacterial agents.

DETAILED DESCRIPTION OF THE PREFERRED EMBODIMENT

An important challenge in regards to antibiotics, is how to avoid the problem of pathological resistance to these medications. By combining two different antibiotics, each having different mechanisms of action, but which work synergistically together this problem can be overcome. The present invention stems from the discovery that certain erythromycin derivatives are easily tolerated by patients without causing gastrointestinal disturbances. Additionally when combined with sulfisoxazole, resistance to Enterococcus Faecalis, methacillin-resistant stapylococci, and erythromycin resistant gram-positive strains is achieved. The inventive combination provides protection from a greater antibacterial spectrum then either erythromycin or sulfisoxazole alone. Thus, this new invention not only saves lives by providing a combination that overcomes medication resistance but is more easily tolerated without stomach upset and vomiting; side effects experienced by many people taking erythromycin alone.

Specifically the basis for the present invention is the pharmaceutical composition of an erythromycin derivative combined with acetylsulfisoxazole according to the structural formulas shown in claim 1 below, where R is hydrogen; C1–C10 alkylcarbonyl, or substituted C1–C10 alkyl wherein said substituent is amino or cyano; and R1 and R2 are independently hydrogen, hydroxyl or amino; and including the pharmaceutical salts and esters thereof. Chemically acetylsulfisoxazole is N-(3,4,-Dimetly-5-isoxazole)-N-sulfanylactamide. Sulfisoxazole, where the acetyl group is replaced by H is an alternative substitution in the invention. Alternative possibilities for the erythromycin derivative include, but are not limited to, the structural formulas as shown in either claim 3 where R is methyl, $R^1$ is H and $R^2$, in claim 5 where R is ammino alkyl carbonyl, $R^1$ is H and $R^2$ is OH, and in claim 6 where R is cyano, $R^1$ is an ammino group, and $R^2$ is H.

In an alternate embodiment, the composition of the present invention may be formulated wherein the erythromycin derivative has the general structural formula as shown below in claim 2, including the pharmaceutically acceptable salts, esters and metal complexes thereof, wherein $R^1$ is hydrogen, C1–C10 alkyl carbonyl or unsubstituted or substituted C1–C10 alkyl wherein the substituent is amino or cyano; $R^2$ and $R^3$ are hydrogen; $R^2$ and $R^3$ together are oxo; $R^4$ is hydrogen or C1–C10 alkylcarbonyl; $R^5$ and $R^6$ are independently hydrogen, hydroxy or amino; $R^5$ and $R^6$ together are oxo or oximino; $R^7$ and $R^8$ are independently hydrogen, C1–C10 alkyl or phenylsulfonyl; $R^9$ is hydrogen, or C1–C10 alkylcarbony, and $R^{10}$ is hydrogen. Examples of operable substitutions for the nine variables include the following:

| $R^1$ | $R^2$ | $R^3$ | $R^4$ | $R^5$ | $R^6$ | $R^7$ | $R^8$ | $R^9$ |
|---|---|---|---|---|---|---|---|---|
| CH3 | H | H | H | H | OH | H | H | H |
| CH3 | H | H | H | H | OH | CH3 | CH3 | H |
| CH3 | H | H | CH3 | H | OH | H | H | H |

In formulating the combination of the present invention it has been found that the mixture ratio by weight, of erythromycin to sulfisoxazole, may range from 100:1 to as much as 1:1, and even trace amounts of sulfisoxazole may be operative. The preferred ratio is 100:38. The erythromycin and sulfisoxazole are prepared following standard laboratory procedures and processes that all competent workers in the field of the present invention will know.

The various alternative formulations of the present invention may take the form of a compressed pill, a powder in an easy to swallow caplet, or even as a fluid dissolved in a liquid such as water. In all cases, the formulation is to be taken orally.

I claim:

1. A pharmaceutical composition containing an erythromycin derivative in combination with an acetylsulfisoxazole according to the structural formulas:

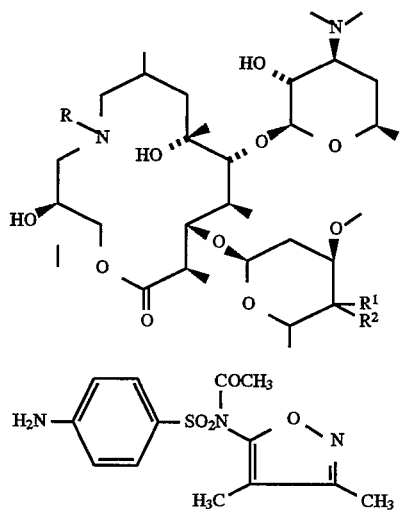

wherein

R is hydrogen, C1–C10 alkylcarbonyl, or substituted C1–C10 alkyl, wherein said substituent is amino or cyano;

$R^1$ and $R^2$ are independently hydrogen, hydroxyl or amino; and pharmaceutical salts and esters thereof.

2. A pharmaceutical composition of a erythromycin derivative combined with acetylsulfisoxazole according to the structural formula:

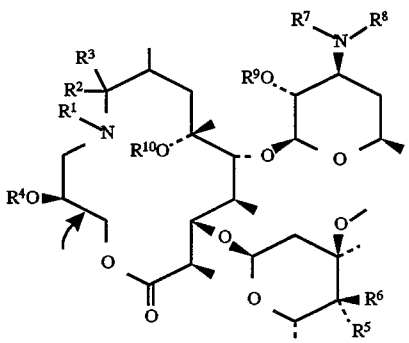

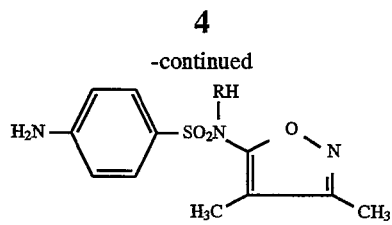

and the pharmaceutically acceptable salts, esters and metal complexes thereof, wherein $R^1$ is hydrogen, C1–C10 alkylcarbonyl or unsubstituted or substituted C1–C10 alkyl wherein said substituent is amino or cyano;

$R^2$ and $R^3$ are hydrogen;

$R^2$ and $R^3$ together are oxo;

$R^4$ is hydrogen or C1–C10 alkylcarbonyl;

$R^5$ and $R^6$ are independently hydrogen, hydroxy or amino;

$R^5$ and $R^6$ together are oxo or oximino;

$R^7$ and $R^8$ are independently hydrogen, C1–C10 alkyl or phenylsulfonyl;

$R^9$ is hydrogen, or C1–C10 alkylcarbony, $R^{10}$ is hydrogen, and $R^{11}$ is hydrogen or acetyl.

3. The composition of claim 1, wherein the erythromycin derivative has the structural formula:

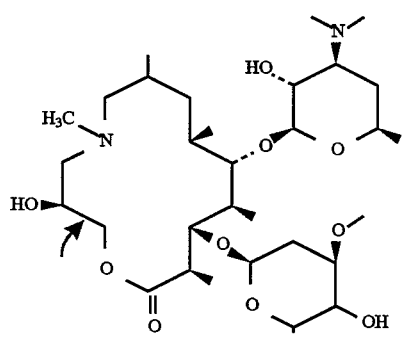

wherein R is methyl, $R^1$ is H and $R^2$ is OH.

4. The composition of claim 1, wherein the erythromycin derivative has the structural formula:

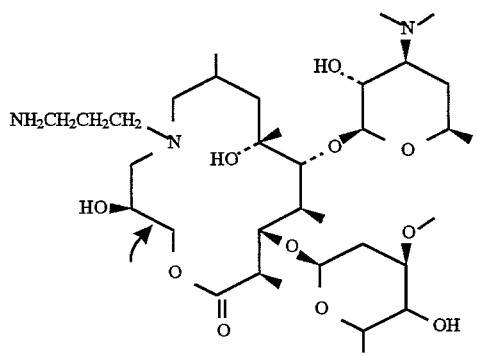
wherein R is amino alkyl carbonyl, $R^1$ is H and $R^2$ is OH.
5. The composition of claim 1, wherein the erythromycin derivative has the structural formula:
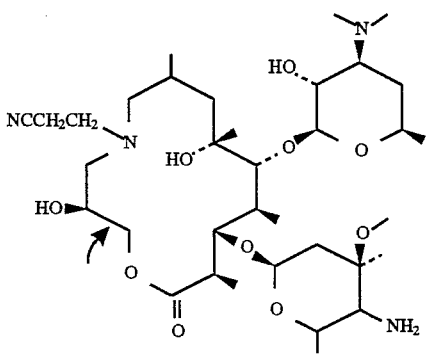
wherein R is cyano, $R^1$ is an amino group, and $R^2$ is H.
* * * * *

UNITED STATES PATENT AND TRADEMARK OFFICE
CERTIFICATE OF CORRECTION

PATENT NO. : 5,641,753  
DATED : June 24, 1997  
INVENTOR(S) : Chris E. Platt

Page 1 of 3

It is certified that error appears in the above-indentified patent and that said Letters Patent is hereby corrected as shown below:

On the cover sheet, delete the title and insert 11-AZA-10-DEOXO-10-DIHYDRO-ERYTHROMYCIN A AND DERIVATIVES COMBINED WITH SULFISOXAZOLE. On the cover sheet, delete the formula structure illustrated in the ABSTRACT, and insert the following new formula structure:

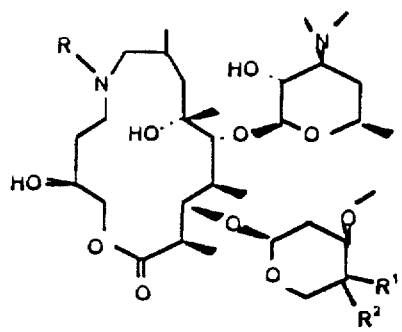 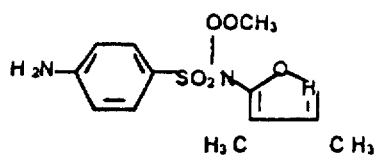

Column 1, line 67, delete "the" and insert --a--; Column 2, line 1, delete "10", and insert --11--. Column 3, lines 15 through 20, delete the formula structure, and insert the following new formula structure:

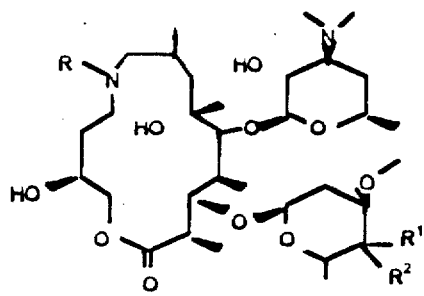 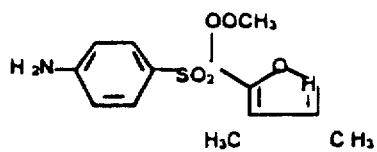

Column 3, lines 46 through 58, delete the formula structure, and insert the following new formula structure:

UNITED STATES PATENT AND TRADEMARK OFFICE
CERTIFICATE OF CORRECTION

PATENT NO. : 5,641,753
DATED : June 24, 1997
INVENTOR(S) : Chris E. Platt

It is certified that error appears in the above-indentified patent and that said Letters Patent is hereby corrected as shown below:

It is certified that error appears in the above-identified patent and that said Letters Patent are hereby corrected as shown below:

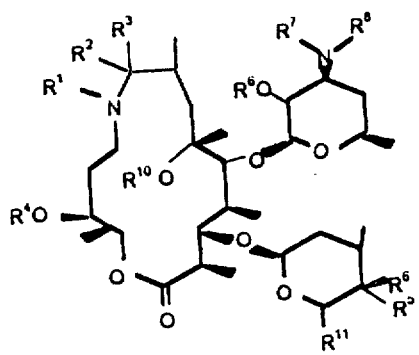

Column 4, lines 37 through 50, delete the formula structure, and insert the following new formula structure:

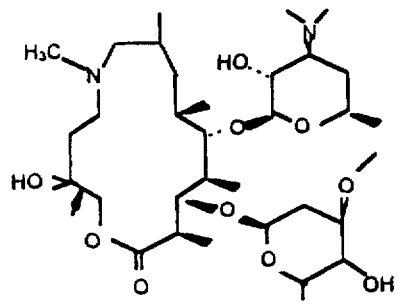

Column 5, lines 1 through 14, delete the formula structure, and insert the following new formula structure:

UNITED STATES PATENT AND TRADEMARK OFFICE
CERTIFICATE OF CORRECTION

PATENT NO. : 5,641,753  
DATED : June 24, 1997  
INVENTOR(S) : Chris E. Platt

Page 3 of 3

It is certified that error appears in the above-indentified patent and that said Letters Patent is hereby corrected as shown below:

It is certified that error appears in the above-identified patent and that said Letters Patent are hereby corrected as shown below:

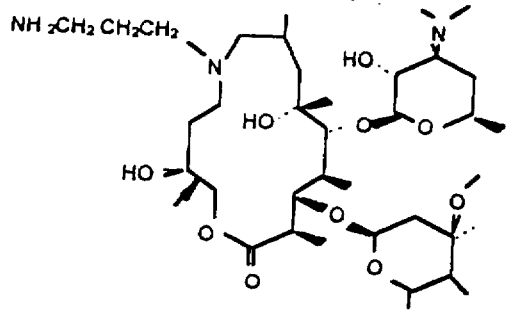

Column 6 lines 1 through 14, delete the formula structure, and insert the following new formula structure:

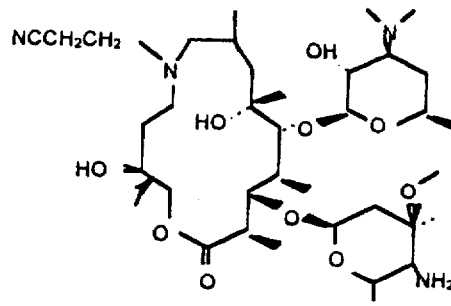

Signed and Sealed this

Eighteenth Day of November 1997

Attest:

BRUCE LEHMAN

Attesting Officer

Commissioner of Patents and Trademarks